US006525101B2

(12) United States Patent
Whiteley

(10) Patent No.: US 6,525,101 B2
(45) Date of Patent: *Feb. 25, 2003

(54) READY-TO-USE GLUTARALDEHYDE CONCENTRATES

(76) Inventor: Reginald Keith Whiteley, 18 Glenside Street, Balgowlah Heights, NSW 2093 (AU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,421
(22) PCT Filed: Oct. 31, 1997
(86) PCT No.: PCT/AU97/00734
§ 371 (c)(1),
(2), (4) Date: Aug. 13, 1999
(87) PCT Pub. No.: WO98/19536
PCT Pub. Date: May 14, 1998

(65) Prior Publication Data
US 2001/0009682 A1 Jul. 26, 2001

(30) Foreign Application Priority Data
Nov. 1, 1996 (AU) .............................................. PO3367

(51) Int. Cl.[7] .......................... A01N 35/00; A01N 25/00; A01N 31/00
(52) U.S. Cl. ........................ 514/698; 514/693; 514/705; 514/724; 514/738; 514/970; 514/974; 514/975
(58) Field of Search ................................. 514/693, 698, 514/709, 724, 738, 970, 974, 975

(56) References Cited

U.S. PATENT DOCUMENTS 3,983,252 A * 9/1976 Buchalter .................... 514/698

FOREIGN PATENT DOCUMENTS

EP 0 407 672 * 1/1991

* cited by examiner

Primary Examiner—Jose' G. Dees
Assistant Examiner—Frank Choi
(74) Attorney, Agent, or Firm—Levisohn, Lerner, Berger & Langsam LLP

(57) ABSTRACT

This invention relates to disinfectant concentrates having improved biocidal activity containing an aldehyde, such as glutaraldehyde, a glycol and a lithium based buffer.

28 Claims, No Drawings

READY-TO-USE GLUTARALDEHYDE CONCENTRATES

This application is a 371 of PCT/AU97/00734, filed on Oct. 31, 1997.

TECHNICAL FIELD

The present invention relates to disinfectant concentrate compositions.

BACKGROUND OF THE INVENTION

New, more efficient machinery recently developed for cleaning, disinfecting and sterilising heat sensitive fibre optical surgical instruments requires a new generation of concentrated glutaraldehyde based instrument disinfectants for optimal operation. A concentrated glutaraldehyde solution is required which is desirably capable of being repeatedly heated to accelerate disinfecting action. Additionally, it is desirable that the solution is diluteable by mechanical means to as low as 0.10 percent glutaraldehyde as part of normal machine operation. To be successful in the market place, the disinfectant is desirably noncorrosive, economical and practical to use in the machinery as well as highly efficient as a disinfectant and chemical sterilant.

Traditional alkaline activated glutaraldehyde disinfectants, now widely used for low temperature disinfecting and sterilising of fibre optical (endoscopic) surgical instruments, are unsuitable for use under heated dilute conditions due to the rapid internal polymerisation of monomeric glutaraldehyde.

In order to attempt to overcome the problems of the prior art, two glutaraldehyde concentrates are presently commercially available for use in new washer-disinfector machines. One concentrate is an undiluted acidic 23 to 25 percent glutaraldehyde concentrate used as manufactured. The second and preferred concentrate is a two component system comprising a first component containing a concentrated 23 to 24 percent glutaraldehyde solution and a phosphate buffer, and a second component containing a surfactant, an optional corrosion inhibitor such as sodium nitrite, and a free alkali to adjust the pH of the two parts when mixed. The two components are mixed to form the working buffered biocidal solution. Both concentrates suffer from the disadvantage that they have limited disinfecting power particularly to mycobacteria, eg Mycobacterium tuberculosis, and to some bacterial and fungal spores as well as some viruses found in whole blood.

The chemistry of glutaraldehyde has been widely described in the literature since its introduction to medical practice as a chemical substitute for heat and ethylene oxide sterilisation. First patented by Pepper, U.S. Pat. No. 3,016,328 in 1962, so called "Activated" glutaraldehyde has become a standard means of sterilising surgical instruments and other complex and heat sensitive surgical instruments. The term "activated", as originally proposed by Pepper, means the pH of the chemical glutaraldehyde whether in its monomeric and/or hydrated forms is adjusted upwards from its stable acidic form to a pH of 7.5 to 9.5 by addition of an "alkalinating" agent in which pH range the biocidal properties of the glutaraldehyde are maximized, in particular its sporicidal activity.

In 1976 Boucher, U.S. Pat. No. 3,969,248 and U.S. Pat. No. 3,968,250 demonstrated that addition of certain non-ionic surfactants to a 2% aqueous glutaraldehyde solution at a pH of 6.3 to 6.5 provided similar "activation", although later findings clearly demonstrated that the degree of "activation" achieved by non-ionic surfactants addition to such mildly acidic glutaraldehyde solutions is less than that achieved by "alkalination" to a pH 7.5 to 9.5. This is believed due to the beneficial affect of the bicarbonate in conjunction with the sodium ion in aiding penetration of glutaraldehyde into bacterial spores. (Scott E. M. & Gomian S. P., Antimicrobial Activity, Uses and Mechanism of Action of Glutaraldehyde, J. Appl. Bacteriol., 1980, 48, 161–190; Scott E. M. & Gorman S. P., Sterilizaton with Glutaraldehyde, in Disinfection, Sterilization and Preservation, 3rd Ed, 1983, Lea & Febiger, pp 65–88). These effects are enhanced at alkaline pH and are optimal at around pH 9.5, above which glutaraldehyde becomes too unstable (polymerises) for use as a practical disinfectant.

Other patents issued in recent years have disclosed the beneficial effect of different surfactants on the biocidal action of dilute glutaraldehyde solutions at alkaline pH, including the divalent metals, calcium and magnesium. However, most surfactants at alkaline pH have received little acceptance in the market place as they have not demonstrated improved biocidal activity of the solutions in practice.

The steady increasing use of glutaraldehyde has been accompanied serious possibility of the development of allergy by users to the strong irritant vapour of glutaraldehyde. In light of this, two patents have disclosed means of decreasing the odour of dilute (1.0 to 3.5%) glutaraldehyde solutions at room temperature by the addition of polyglycols which can be shown to hydrogen bond to the dialdehyde. U.S. Pat. No. 4,436,754 (Taylor) demonstrated that at a pH of 7.5 to 9.5 (achieved by separate alkalination prior to use), glycols containing from 1 to 22 ethylene oxide groups were effective in suppressing the odour of chemical sterilants by reducing the vaporisation of glutaraldehyde. This product was, of necessity, supplied in two parts, one part containing a stabilised acidic glutaraldehyde-glycol complex and the second part containing a lesser quantity of buffer alkaline salts, surfactants and corrosion inhibitors. AU 562,017 (Whitely et al) and NZ 204,717 disclosed a stable near neutral chemical sterilant containing triethylene glycol and 1 to 2.5% glutaraldehyde. This was successfully marketed as Wavicide AID with greatly reduced odour compared with "alkalinated" glutaraldehyde preparations and a demonstrated reduced incidence of odour complaints and allergy reactions from regular uses of "alkalinated" glutaraldehyde based instrument sterilants. However, like all known alkalinated 2% glutaraldehyde preparations, this formulation was subsequently demonstrated to be less effective than claimed for killing mycobacterium, in particular Mycobacterium tuberculosis, which as a group of pathogens is assuming major significance as a complimentary infection in immune-depressed AIDS/HIV patients.

Subsequently, AU 589,267, (Whiteley) taught that a specific interaction occurs between a hydrogen bonded complex formed between 1.0 to 1.5 mole of triethylene glycol and 1 mole of monomeric glutaraldehyde when mixed with certain non-ionic surfactants. Small quantities of the non-ionic surfactants were reacted with the glutaraldehyde-glycol complex with a corresponding loss of surface activity as measured by change in the air/water surface tension of aqueous solutions. The resulting three part complex significantly enhanced the overall effectiveness of glutaraldehyde as a biocide in the pH range 6.0 to 7.5, especially against mycobacterium. Increase in biocidal action was achieved while still effectively reducing the vaporisation of glutaraldehyde. Killing time against mycobacteria was reduced at room temperature from 20 to 45 minutes for 2% "alkalinated" glutaraldehyde preparations to 5 to 10 minutes for the new three part complex in a 2% glutaraldehyde preparation. The complex was subsequently marketed under trade name AIDAL PLUS.

Patent literature also reveals many other attempts to improve the mycobiocidal effectiveness of 1 to 3.5% aqueous glutaraldehyde solutions. For example, U.S. Pat. No. 4,923,899 (Wachman) describes a composition comprising glutaraldehyde, a quaternary biocide, low molecular weight glycols and alcohols, monovalent metal nitrate, sulphite and chlorites and a chelating agent.

U.S. Pat. No. 5,252,606 (Martin) teaches the fortification of glutaraldehyde preparations by addition of a quaternary biocide, as well as a para tertiary amyl phenol, citric acid and isopropanol. The formulation disclosed contains 46% w/w of water in addition to other ingredients. Based on experience with similar experimental formulae such mixtures are subject to limited shelf life due to progressive loss of monomeric glutaraldehyde on storage, presumably as the formulation does not appear inhibited against internal polymerisation of glutaraldehyde. Research has clearly demonstrated that mycobiocidal activity of glutaraldehyde is seriously restricted by the presence of a significant quantity of a quaternary biocide together with phenols which, literature reports, may also serve to reduce the effectiveness of phenolic biocides.

U.S. Pat. No. 5,322,856 (Martin) teaches the incorporation of a second phenolic biocide and a second quaternary biocide to the preparation disclosed in U.S. Pat. No. 5,252,606. This has the effect of significantly altering the respective ratios of the three biocides. Triethanolamine together with a small quantity of triethanolamine hydrochloride is also added as a solubilizing agent to hold the product together. The presence of a larger quantity of quaternary biocides makes the new mixture a high foaming material which limits its use in health care. In addition the presence of a large quantities of phenolic biocide in an acidic environment increases problems of chemical action on plastic and plastic coated surfaces which are widely used in medical practice, particularly as internal surfaces of fibre optical surgical instruments. Its potential for serious occupational health and safety problems is also significantly enhanced. Because of the presence of phenols it cannot be heated without potentiating further damage to organic and plastic surfaces as well as causing an occupational health hazard.

None of the formulations in U.S. Pat. No. 5,252,606 or U.S. Pat. No. 5,322,856 appear suitable for use as diluteable concentrates at room temperature or heated for medical chemical sterilisation or high level disinfection of complex highly expensive fibre optical surgical instruments.

Other parents include AU-A 667878/87 (Ascenzi et al) which teaches mixtures of 0.3 to 6.0% glutaraldehyde and 0.01 to 6.0% of a nominated conjugated monoaldehyde for improving the kill rate of glutaraldehyde to mycobacterium. These preparations require "alkalination" before use. Such alkalinated glutaraldehyde solutions do not remain stable under heat with currently disclosed technology. In addition, no evidence has been presented of the effectiveness or biocidal action of the formulations at concentrations as low as 0.10% glutaraldehyde, a definite requirement for use in washer-disinfectant steriliser machines.

Another patent WO 91/16083, (Boucher) teaches forming a two part glutaraldehyde concentrate. A first major part is a solution of from 20 to 25% glutaraldehyde which is pH adjusted with acidic phosphates to pH 5.5 to 6.0 for maximum stability. The first part also contains not more than 2.5% non-ionic surfactants. Before use, the concentrate is "activated" by addition of an alkaline mixture of sodium hydroxide and sodium nitrite at a concentration such that when mixed with the acidic glutaraldehyde concentrate, a pH of 6.2 to 6.4 is obtained in the resultant ready-to-use solution. This concentrate is an example of two part glutaraldehyde preparations currently available commercially for use in heated washer-disinfectors sterilisers now in increasing use. The formulation is currently under challenge with respect to its claims of myobacteriacidal activity at room temperature (20 degrees Celsius).

From the above it is clearly seen that a new glutaraldehyde concentrate is needed which fulfills a number of requirements. A commercially viable concentrate of glutaraldehyde is needed which desirably is chemically stable for a minimum period of two years, with a maximum loss of titrateable glutaraldehyde monomer of 10%. Further, although the maximum stability of a glutaraldehyde/non-ionic surfactant mixture lies at a pH around 5.0, to achieve maximum biocidal effectiveness a diluted solution of a glutaraldehyde concentrate desirably has a pH lying in the range 6.0 to 9.5. In order to achieve this pH range, the pH of a ready-to-use diluteable concentrates will desirably have a pH of 6.0 or above, preferably around 6.5 to 7.5 and accordingly a glutaraldehyde concentration is needed which is capable of fulfilling this requirement without decomposition. In this regard glutaraldehyde becomes progressively more unstable due to internal polymerisation at pH's above 6.5, with instability increasing as the pH rises.

A major problem is therefore how to prevent a concentrated glutaraldehyde preparation with a pH in excess of 6.2 from deteriorating by internal polymerisation over a prolonged storage period, under ambient temperature conditions, to an extent of no more than 10 percent over two years at room temperature. The reactions that promote internal polymerization of glutaraldehyde at a pH in excess of 5.0 are believed due to the following factors. Firstly the presence of free water which provides a vehicle for oxidative polymerisation reactions involving ion transfer (in the absence of free water it is far less likely that such ionising reactions will occur). Secondly oxidative reactions cause the pH of aqueous solutions of glutaraldehyde to decrease steadily on storage, presumably due to the development of glutaric or similar acids being formed along the pathway to internal polymerisation of monomeric glutaraldehyde.

It would also be desirable to find a buffer system soluble in the concentrate that will be effective over the desired pH range and which will maintain a pH above 6.0 at dilutions as low as 0.125% glutaraldehyde, this being the lowest dilution required by latest version washer-disinfector machinery being heavily promoted in Europe.

It would also be desirable to find an improved glutaraldehyde concentrate which can be used as manufactured i.e. one that does not require premixing of unpleasant and toxic glutaraldehyde by health care workers before use and which still demonstrates high effectiveness against bacteria, fungi and blood borne viruses, particularly hepatitis B and C and the AIDS virus in whole blood. These particular pathogens are being spread increasingly in populations around the world by transfer of whole blood and body fluids through, for example, drug use, trauma events, surgical procedures and sexual practices.

It is the object of the present invention to overcome or ameliorate at least some of the abovementioned deficiencies of the prior art.

SUMMARY OF THE INVENTION

According to a first aspect the invention consists in a stable disinfectant concentrate comprising:

a) at least one mono or dialdehyde containing 2 to 11 carbon atoms;

b) at least one glycol or polyol containing 2 to 10 carbon atoms; and c) at least one lithium based buffer soluble in said concentrate and capable of maintaining the concentrate at pH 6 or above.

In highly preferred embodiments the concentrate according to the first aspect further comprises an anionic or non ionic surfactant.

According to a second aspect the invention consists in a method of disinfection and/or sterilisation comprising the step of contacting a surface with a disinfectant concentrate according to the first aspect for a period of time sufficient to achieve disinfection and/or sterilisation.

According to a third aspect the invention consists in a method of preparing a stable disinfectant concentrate comprising the steps of combining;

a) at least one mono or dialdehyde containing 2 to 11 carbon atoms;

b) at least one glycol or polyol containing 2 to 10 carbon atoms;

c) at least one lithium based buffer soluble in the concentrate and capable of maintaining the concentrated solution at a pH 6 or above.

According to a fourth aspect the invention consists in a diluted disinfectant comprising a concentrate according to the first aspect and a diluant.

According to a fifth aspect the invention consists in a method of disinfection or chemical sterilization of an object comprising the step of contacting said object with a diluted disinfectant according to the fourth aspect.

DESCRIPTION OF PREFERRED EMBODIMENTS

The present invention provides disinfectants which are stable. In certain preferred embodiments the concentrate is stable under normal storage conditions for a minimum of two years, the concentrate losing not more than 10 percent of its initial titrateable aldehyde during the period of storage. The concentrates of the invention are capable of being diluted before use preferably with water or lower alkanol or a mixture thereof preferably to a mono or dialdehyde content of 0.05 to 3.5 percent by weight on the diluted concentrate. The diluted concentrate preferably has a pH ranging from 6.0 to 8.0. In certain preferred embodiments the diluted concentrate is capable of being heated to 55° C. (to provide fast sterilising times) without decomposition or loss of biocidal activity. In this regard the diluted concentrates according to certain preferred embodiments of the invention have sporicidal, fungicidal, mycobiocidal, bacteriocidal and virucidal activity.

In one preferred embodiment the invention provides a chemically stable product containing from 21 to 24 percent by weight of monomeric gluteraldehyde requiring no pre-mixing before use. The concentrates of the invention have other uses in hygiene and in some industrial processes, including air conditioning where fast efficient disinfecting processes are required, particularly those which are mechanically controlled.

The concentrates of the invention contain a mono or dialdehyde and a glycol. It is known that glutaraldehyde will form hydrates, each carbonyl group adding a molecule of ionised water. Similarly glutaraldehyde can form a hydrogen bonded complex with up to four molecules of glycol. Glycols, particularly those of lower molecular weight, can also bind water by hydration probably more effectively than glutaraldehyde. Thus if a fifty percent (50%) aqueous solution of glutaraldehyde and anhydrous triethylene glycol are mixed in appropriate molar quantities it is expected that the water of hydration would be displaced in whole or in part from glutaraldehyde in favour of binding to the glycol of the resultant aldehyde-glycol complex so formed. This restricts the possibility of free ion transfer reactions with the solution, specially those involved in the internal polymerisation of hydrated glutaraldehyde. Published classical theory suggests monomeric glutaraldehyde to first fully hydrate as an initial step in oxidative mechanisms leading to polymer formation, which can occur by either of two alternative pH dependent means.

Indeed this is what happens in practice of the present invention. In this regard a molecular ratio of 1 mole of glutaraldehyde and 0.75 to 1.5 mole of triethylene glycol forms a chemically stable solution. To further limit the possibility of oxidative polymerisation either in storage or in use when exposed to air, it is preferable to further add an anti-oxidant or organic reducing agent effective in the pH range of 5.5 to 7.5 is also advisable. A suitable antioxidant is ascorbic acid which if necessary is pH adjusted. Other organic antioxidants can be used such as hydroquinone derivatives and propyl gallate. Typically the antioxidant is present in an amount of from 0.01 to 2.5 percent, more preferably 0.01 to 1 percent, by weight of the concentrate. Preferably the antioxidant or organic reducing agent is in the form of a salt, preferably its lithium salt. Ascorbic acid salts are most preferred on grounds of toxicology, chemical stability, freedom from colour development and absence of odour as well as being proven as anti-oxidants possessing free-ion scavenging ability in complex biological systems of relevance.

Although the predominant discussion in this patent specification relates to the use of glutaraldehyde, other mono, di or conjugated monalkyl and aromatic aldehydes containing less than 11 carbon atoms can be used. The mono or dialdehyde is preferably present in an amount of from 10 to 35 percent by weight of the concentrate. Similarly glycols other than triethylene glycol can be used in the invention including those containing 2 to 10 carbon atoms such as ethylene glycol, diethylene glycol and, tetraethylene glycol, or other highly polar polyols including some nonionic surfactants. The use of a lower alkanol such as ethanol and isopropanol in part substitution of the glycol also yields solutions which have reasonable stability. However, the lower alkanols may give off unwanted odours and may be flamable in circumstances that should be avoided in areas where the principal uses of the glutaraldehyde concentrate are found in medical and veterinary practice.

The concentrates of the invention further contain a buffer required to control the pH of both the concentrate and its dilutions to within the desired biocidal effective range, which in the present invention is 6 or above, more preferably in the range of from 6 to 9.5. In the present invention a lithium based buffer is used as it has been found unexpectedly that such buffers enhance the biocidal action of the concentrate. Suitable lithium based buffers include organic lithium salts of hydroxyorganic or organic acids containing from 2 to 8 carbon atoms, lithium salts of phosphoric acid or mixtures thereof. The lithium based buffer can be used in combination with other buffers for example one or more other monovalent metal salts of a hydroxyorganic or organic acid containing from 2 to 8 carbon atoms and/or monovalent metals salts of phosphoric acid. A lithium citrate based buffer or mixtures of potassium and lithium citrate are preferred. Lithium citrate is most preferred. Suitably the buffer is used at a concentration of 0.1 to 2.5% w/w of the concentrate, preferably 0.1 to 1% w/w most preferably 0.3 to 0.5% w/w, particularly when a lithium citrate buffer is used. The addition of ascorbic acid as an antioxidant contributes to the effectiveness of the lithium based buffers. Other organic acid buffers can also be employed in addition to the lithium based buffer for example, glycolic acid, lactic acid and acetic acid, benzoic acid, salicylic acid, phthalic acid, phenolsulphonic acid, and mixtures thereof. Again lithium salts and potassium salts of these organic acid buffers and mixtures thereof are preferred for optimal biocidal action.

Preferably the concentrates of the invention further contain a surfactant. The surfactant is desirably chosen to maximise the biocidal action of the gluteraldehyde concentrates. Suitable surfactants include anionic and non-ionic surfactants or mixtures thereof such as those described in Australian patent 589,267 (which disclosure is incorporated herein by reference). Preferably the surfactant is in the form of its monovalent metal salt, more preferably its lithium salt. The surfactant is typically present in an amount of from 0.1 to 7.5% by weight of the concentrate. Mixtures of nonionic surfactants together with the lithium salts of either sulphated and sulphonated (C8 to C16) alkyl alcohols or alkyl hydrocarbons or (C6 to C16) alkyl aromatic sulphonates and alkyl diphenyl oxide mono and disulphonates are preferred. When a mixture of nonionic and anionic surfactants are used they can be used in the proportions of 10% to 90% anionic surfactant to 10% to 90% nonionic surfactant, dependent upon the specific micelle equilibrium required. The acid form of the surfactant, provided chemically stable, can additionally act as pert of a buffer.

Suitable aqueous solvents include water or a lower alkanol.

The invention will now be described with reference to the following examples.

EXAMPLE 1

Concentrates in accordance with the invention were prepared and diluted to glutaraldehyde concentrations of 2.0–2.2% w/w and 0.125%. The buffer used was lithium citrate used at a concentration of 0.1 to 1.0 percent by weight of the undiluted concentrate. The pH of each formulation was determined. The results are shown in Table 1 below.

TABLE 1

BUFFER CAPACITY OF LITHIUM CITRATE

| Glutaraldehyde Concentration | 22.5% | 2.0–2.2% | 0.125% |
|---|---|---|---|
| pH Freshly made | 7.1 | 6.8 | 6.5 |
| pH @ 3 months @ 40° C. | 6.9 | 6.6 | 6.2 |

Over a three month storage period at 40° C., equivalent to 1 year at room temperature, the loss of titrateable glutaraldehyde monomer of these formulations amounted to only 0.8 percent. This approximates to 1.6 percent or 7.5 percent loss over two years.

EXAMPLE 2

Analytical testing of glutaraldehyde concentrates of the invention performed using a standard hydroxylamine titration method (in which reaction between glutaraldehyde and hydroxylamine releases hydrochloric acid which is back titrated potentiometrically) show that a lithium citrate based buffer results in a quicker reaction rate (release of HCl) and a lower pH (0.9 compared to 1.5) than that of a sodium-potassium phosphate buffer of similar concentration such as used in most commercial 2 to 3.5 percent glutaraldehyde based instrument disinfectants. This, it appears from biocidal testing, corresponds to fast killing times for some micro-organisms when using concentrates in accordance with the invention than is achieved by conventional 2 to 3.5 percent glutaraldehyde preparations containing sodium-potassium phosphate buffers.

EXAMPLE 3

Two formulations in accordance with the present invention were prepared:

| | A | B |
|---|---|---|
| Glutaraldehyde, 50% | 480 grams | 480 grams |
| Triethylene glycol | 460 grams | 460 grams |
| Teric 12A8* | 15 grams | 35 grams |
| Lithium lauryl sulphate | 35 grams | — |
| Lithium alkyl benzene sulphonate | — | 15 grams |
| Lithium citrate | 1.5 grams | 2.0 grams |
| Potassium citrate | 1.0 gram | — |
| Lithium ascorbate | 0.35 grams | 0.75 grams |
| TOTAL | 1,000 grams | 1,000 grams | pH adjust to 7.0 to 7.2 with 10% lithium hydroxide
*Manufactured by ICI Australia Limited Both formulations were extensively tested microbiologically against medially significant microbes and compared with a product manufactured according to Australian patent 589,267 known commercially as AIDAL PLUS. The organisms tested for biocidal activity were as follows:

| Bacteria | Psuedomonas aeruginosa |
| | Proteus vulgaris |
| | Escherichia coli |
| | Staphylococcus aureus |
| Bacterial spore | Bacillus subtilis |
| Mycobacteria | Mycobacterium tuberculosis |
| Virus | AIDS virus HIV in whole blood |
| | Hepatitis DHBV in whole blood |

These organisms represent a recognised and accepted spectrum of the important medially significant pathogens found in hospitals, health care facilities and the general community. In each case there was either no discernible difference or a distinct improvement in biocidal effectiveness to the commercial product AIDAL PLUS at equivalent concentrations of glutaraldehyde. According to literature AIDAL PLUS is more effective known 2% w/w glutaraldehyde containing hospital instrument disinfectant and chemical sterilant.

When heated to 45° C. the formulations of the invention passed the Australian TGA Disinfectant Test, Option B, Soiled Conditions, (yeast challenge) at a concentration of 0.125 percent glutaraldehyde. They also killed Mycobacterium tuberculosis in less than 5 minutes at room temperature at a 2% w/w glutaraldehyde concentration, which qualifies under the recent Australian Therapeutic Goods Authority (TGA)—Therapeutic Goods Order No 54 regulations as both a High Level Instrument Disinfectant and Sterilant suitable for use in fibre optical instruments use in invasive surgery in sterile body tissue. Other data qualify the biocidal results of these concentrates for acceptance as a chemical sterilant, the highest level of biocidal effectiveness required by regulatory authorities in most countries.

An example of the amplification of biocidal action achieved by the formulations of the invention is shown below as the rate of kill of chemically resistant bacterial spores of Bacillus subtilis compared with the sporicidal action of AIDAL PLUS at 20 degrees Celsius.

| PRODUCT | AIDAL PLUS | FORMULA A | FORMULA B |
|---|---|---|---|
| KILL TIME, minutes | Less than 180 | Less than 90 | Less than 120 |

The time to kill this particular bacterial spore is taken universally as the time a chemical takes to sterilise an object. This time is critical when expensive and complex surgical instruments are to be sterilised between use and the most rapid turn around time possible is sought. As will be noted the formulations of this invention are superior in this respect to forerunner products and represent a major commercial and practical advance in the sterilisation of surgical and veterinary equipment.

It will be obvious to those well versed in the art that modifications of the typical formulations herein are possible within the scope and principles disclosed in this specification. All such variations are considered within the scope of this patent disclosure.

What is claimed is:

1. A stable disinfectant non-aqueous concentrate comprising:
   a) at least one mono or dialdehyde containing 2 to 11 carbon atoms;
   b) at least one glycol or polyol containing 2 to 10 carbon atoms; and,
   c) at least one lithium-based buffer soluble in said concentrate;
   d) wherein said glycol or polyol are present in a molar ratio of said glycol or polyol to said mono or dialdehyde to sufficiently displace the water of hydration from binding to said mono or dialdehyde in favor of binding to said glycol or polyol, wherein the concentrate contains substantially no free water such that deterioration of the mono or dialdehyde by internal polymerisation is no more than 10 percent over two years at room temperature and wherein said concentrate is maintained at a pH of about 5 or above.

2. The concentrate according to claim 1 further comprising an anionic or non ionic surfactant.

3. The concentrate according to claim 1 wherein the mono or dialdehyde is a mono, di or conjugated monoalkyl or aromatic aldehyde.

4. The concentrate according to claim 1 wherein the mono or dialdehyde is glutaraldehyde.

5. The concentrate according to claim 1 wherein the mono or dialdehyde is present in an amount of from 10 to 35 percent by weight of the concentrate.

6. The concentrate according to claim 1 wherein the glycol is selected from the group comprising triethylene glycol, ethylene glycol, diethylene glycol, tetraethylene glycol or mixtures thereof.

7. The concentrate according to claim 6 wherein the glycol is triethylene glycol.

8. The concentrate according to claim 1 wherein the glycol or polyol is present in molecular ration of 0.75 to 1.5 moles of glycol for each mole of aldehyde.

9. The concentrate according to claim 1 wherein the lithium based buffer is selected from the group comprising an organic lithium salt of an hydroxyorganic or organic acid containing from 2 to 8 carbon atoms or a lithium salt of phosphoric acid or mixtures thereof, said lithium based buffer optionally in combination with one or more other monovalent metal salts of a hydroxyorganic or organic acid containing from 2 to 8 carbon atoms or monovalent metal salt of a phosphoric acid.

10. The concentrate according to claim 1 wherein the lithium based buffer is lithium citrate used alone or in combination with potassium citrate.

11. The concentrate according to claim 1 wherein the lithium based buffer is present in an amount of from 0.1 to 2.5 percent by weight of the concentrate.

12. The concentrate according to claim 1 wherein the concentrate has a pH ranging from 6 to 9.5.

13. The concentrate according to claim 2 wherein the surfactant is an anionic surfactant.

14. The concentrate according to claim 13 wherein the surfactant is a monovalent metal salt of an anionic surfactant.

15. The concentrate according to claim 14 wherein the surfactant is the lithium salt of an anionic surfactant.

16. The concentrate according to claim 13 wherein the surfactant is present in an amount of from 0.1 to 7.5% by weight of the concentrate.

17. The concentrate according to claim 1 further comprising an antioxidant or an organic reducing agent.

18. The concentrate according to claim 17 wherein the antioxidant is selected from ascorbic acid, hydroquinone derivatives or propyl gallate.

19. The concentrate according to claim 17 wherein the antioxidant or organic reducing agent is in the form of its lithium salt.

20. The concentrate according to claim 17 wherein the antioxidant or organic reducing agent is present in an amount of from 0.01 to 2.5 percent by weight of the concentrate.

21. The concentrate according to claim 1 wherein part of the glycol is replaced with a lower alkanol.

22. The concentrate according to claim 21 wherein the lower alkanol is selected from ethanol or isopropanol.

23. The concentrate according to claim 1 further including a solvent.

24. The concentrate claimed in claim 1, wherein said lithium-based buffer maintains said concentrate at a pH in the range of about 6 to 9.5.

25. A method of disinfection and/or sterilization comprising the step of contacting a surface with a disinfectant concentrate according to claim 1 for a period of time sufficient to achieve disinfection and/or sterilization.

26. A method of preparing a stable disinfectant concentrate comprising the steps of combining;
   a) at least one mono or dialdehyde containing 2 to 11 carbon atoms;
   b) at least one glycol or polyol containing 2 to 10 carbon atoms; and
   c) at least one lithium-based buffer soluble in said concentrate;
   d) wherein said glycol of polyol is present in a molar ratio of said glycol or polyol to said mono or dialdehyde sufficient to substantially displace the water of hydration from binding to said mono or dialdehyde in favor of binding to said glycol or polyol, wherein the concentrate contains substantially no free water and wherein said concentrate is maintained at a pH of about 5 or above.

27. The method claimed in claim 26, wherein said lithium based buffer maintains said concentrate at a pH in the range of about 6 to 9.5.

28. A diluted disinfectant comprising a concentrate according to claim 1 and a diluant wherein the mono or dialdehyde is present in an amount of from 0.05 to 3.5 percent by weight of the diluted disinfectant.

* * * * *